United States Patent
Burns

(10) Patent No.: US 7,964,225 B1
(45) Date of Patent: Jun. 21, 2011

(54) TEAR STAIN MANAGEMENT COMPOSITIONS AND METHODS

(75) Inventor: Catherine M. Burns, Nanuet, NY (US)

(73) Assignee: Naturally Tearfree Canine, LLC, Nanuet, NY (US)

( * ) Notice: Subject to any disclaimer, the term of this patent is extended or adjusted under 35 U.S.C. 154(b) by 0 days.

(21) Appl. No.: 12/791,317

(22) Filed: Jun. 1, 2010

Related U.S. Application Data

(60) Provisional application No. 61/224,251, filed on Jul. 9, 2009.

(51) Int. Cl.
*A61K 36/9066* (2006.01)
*A61K 36/00* (2006.01)
*A23K 3/00* (2006.01)

(52) U.S. Cl. .......................... 424/756; 426/53; 424/725

(58) Field of Classification Search .................. None
See application file for complete search history.

(56) References Cited

U.S. PATENT DOCUMENTS

| | | | |
|---|---|---|---|
| 2003/0113390 A1* | 6/2003 | Hoie | 424/757 |
| 2005/0112217 A1 | 5/2005 | Khoo | |
| 2006/0193928 A1* | 8/2006 | Soman et al. | 424/725 |
| 2009/0274660 A1 | 11/2009 | Girsh | |

* cited by examiner

*Primary Examiner* — Qiuwen Mi
(74) *Attorney, Agent, or Firm* — Bachman & LaPointe, P.C.

(57) ABSTRACT

An animal dietary supplement composition comprises effective amounts of basil and turmeric for tear stain reduction.

6 Claims, No Drawings

TEAR STAIN MANAGEMENT COMPOSITIONS AND METHODS

CROSS-REFERENCE TO RELATED APPLICATION

Benefit is claimed of U.S. Patent Application Ser. No. 61/224,251, filed Jul. 9, 2009, and entitled "Tear Stain Management Compositions and Methods", the disclosure of which is incorporated by reference herein in its entirety as if set forth at length.

BACKGROUND

The invention relates to management of tear stains (e.g., in dogs). More particularly, the invention relates to nutritional/dietary supplements for assisting in such management.

Tear staining has been a significant problem in dogs and cats. It has been a particular problem in certain light coated breeds where the stains are more visible. Bacterial infection is believed behind increased tearing and resultant stains.

There have been a number of attempts to treat such tearing. One antibiotic treatment is tylosin which is a macrolide-class antibiotic.

SUMMARY OF THE INVENTION

An alternative to tylosin-based treatments is desirable. Thus, one aspect of the invention involves an inventive supplement composition comprising effective amounts of: basil and turmeric. It may be delivered in powder form, more particularly added to food directly prior to feeding. It may be packaged with use directions.

Another aspect of the invention involves a method of tear stain management for an individual canine comprising orally administering to the canine amounts of basil and turmeric. An exemplary quantity is at least 0.2 g basil and at least 0.2 g turmeric in a given day.

DETAILED DESCRIPTION

The inventive supplement composition comprises effective amounts of basil (e.g., powdered) and turmeric (e.g., also powdered) to control animal (e.g., canine) tear stains. It may be delivered in powder form. A specific example follows.

Basil is a leaf: *ocimum basilicum*. It is believed that basil has anti-bacterial and anti-fungal activity. In published studies basil essential oils and their principal constituents were found to exhibit antimicrobial activity against a wide range of Gram-negative and Gram-positive bacteria, yeast, and mold. It may further have anti-tumor activity. One study shows basil leaf to inhibit carcinogen-induced tumors.

Turmeric is a root: *curcuma longa*. Turmeric contains curcumin and curcuminoids, which are powerful anti-inflammatory phytochemicals that are believed to act as natural cyclooxygenase-2 (COX-2) inhibitors in the body, and inhibit the production of the prostaglandins that cause inflammation and swelling. Turmeric is a natural antioxidant, and thus protects the body from oxidative damage. Laboratory studies have found that turmeric inhibits the development of cataracts.

An exemplary content is 50% each basil and turmeric powder, by weight. Exemplary packaging is plastic or glass jar containing 4 oz wt., more broadly, 2-8 oz wt. An exemplary content is tylosin-free or essentially tylosin-free (e.g., having levels below that required for significant tear control effect alone).

Both ingredients are FDA approved and on the GRAS list. Exemplary ingredients are obtained as powder stock and mixed. Exemplary ingredients are organically farmed. Although the effect of basil may be more significant than turmeric, it is believed that there is a combined/synergistic effect.

Exemplary usage is sprinkled onto and mixed with canned dog food directly prior to feeding once per day. An exemplary recommended/label dosage follows a 3-2-1 rule: first week use for 3 days in a row, 2nd week use 2 days in a row, 3rd week use one day. After three weeks, use for one day once a month indefinitely/maintenance. For dogs under 20 lbs, give ¼ teaspoon each time, dogs over 20 lbs, give ½ teaspoon each time. An exemplary weight of the quarter teaspoon of the 50-50 mixture is believed about 0.58 g. Thus, an exemplary dosage would involve about 0.3 g each of the basil and turmeric, more broadly, at least 0.2 g or 0.2-1 g.

Directions (e.g., a, label, insert, and/or box graphic) accompanying a package (e.g., a bottle/jar) may identify said suggested usage.

Testing of the 50-50 powder composition with the label dosage described above has been observed to markedly reduce visible tear staining in a variety of dogs. The reduction is believed primarily to result from a reduced content of stain-formers in tears rather than reduced tearing volume. An additional observed benefit has been a reduction in the effects of dog urine on lawns (reduced grass bleaching/kill). This may be due to an effect of neutralizing/reducing urine acidity.

One or more embodiments of the present invention have been described. Nevertheless, it will be understood that various modifications may be made without departing from the spirit and scope of the invention. For example, alternative delivery vehicles such as edible chews, capsules/pills/tablets, and the like are possible. Accordingly, other embodiments are within the scope of the following claims.

What is claimed is:

1. A method of tear stain management for an animal in need thereof, said method comprising orally administering to the animal daily effective amounts of basil and turmeric.

2. The method of claim 1 wherein:
said amounts are administered in a decreasing frequency dosage.

3. The method of claim 1 wherein:
said amounts are administered via mixing with food.

4. The method of claim 1 wherein:
said animal is a dog.

5. The method of claim 1 wherein:
said amounts are at least 0.2 g of each of said basil and said turmeric in a given day.

6. The method of claim 1 wherein:
said amounts are at least 0.2 g of each of said basil and said turmeric in a given feeding.

* * * * *